United States Patent [19]
Mautone

[11] Patent Number: 5,306,483
[45] Date of Patent: * Apr. 26, 1994

[54] PHOSPHOLIPID DELIVERY SYSTEM

[75] Inventor: Alan J. Mautone, Morris Township, Morris County, N.J.

[73] Assignee: Scientific Development & Research, Inc., Belleville, N.J.

[*] Notice: The portion of the term of this patent subsequent to Dec. 29, 2009 has been disclaimed.

[21] Appl. No.: 940,496

[22] Filed: Sep. 4, 1992

Related U.S. Application Data

[63] Continuation-in-part of Ser. No. 385,907, Jul. 27, 1989, Pat. No. 5,174,988.

[51] Int. Cl.⁵ ................................................ A61K 9/12
[52] U.S. Cl. ...................................... 424/45; 424/450
[58] Field of Search .................................... 424/45, 450

[56] References Cited

U.S. PATENT DOCUMENTS

| | | | |
|---|---|---|---|
| 4,370,349 | 1/1983 | Evans et al. | 424/450 |
| 4,394,372 | 7/1983 | Taylor | 424/450 |
| 4,508,703 | 4/1985 | Redziniak et al. | 424/45 |
| 4,973,465 | 9/1990 | Baurain | 424/406 |

*Primary Examiner*—Thurman K. Page
*Assistant Examiner*—Raj Bawa
*Attorney, Agent, or Firm*—Frank Cozzarelli, Jr.

[57] ABSTRACT

A process to prepare lipid crystalline figures in chloro or hydro fluorocarbon propellants or mixtures thereof for the aerosol delivery of therapeutically active substances which form amorphous films on delivery and which can be suspended in aqueous media to serve as a drug delivery system or, when used without therapeutically active substance, as an artificial tear.

20 Claims, No Drawings

PHOSPHOLIPID DELIVERY SYSTEM

This patent application is a continuation-in-part of application serial number 385,907 filed on July 27, 1989, now U.S. Pat. No. 5,174,988, issued on Dec. 29, 1992.

FIELD OF INVENTION

This invention relates to compositions which are useful in the fields of (1) pharmaceutical or drug delivery, both by aerosolization into mammalian lungs, but is not limited to these organs, in non-aqueous medium and by drops into the eyes in aqueous media, but is not limited to these organs, and (2) artificial tears. A further aspect of this invention is directed to the process for preparing the delivery system, and the artificial tears.

DESCRIPTION

Background of Invention

The present invention has a wide range of usefulness in biomedicine. It serves as a vehicle for drug administration both into the lungs and into the eyes; in addition, the eye vehicle itself, without drugs, serves as artificial tears.

Two of the body's epithelial surfaces that are in direct contact with ambient air are the surfaces of the lung (airways and alveoli) and of the eyes (cornea-conjunctiva). Each of these surfaces is covered by an acellular, essentially two-phase fluid system: the external phase, or layer, which interfaces with air, is lipidic and the internal phase or layer, which interfaces with tissue, is aqueous. A third layer possibly equivalent to the glycocalyx of other structures, is probably more closely bound to the epithelial surface and may be composed of carbohydrates and proteins.

Traditionally, pharmaceuticals, drugs and therapeutic materials have been administered to the body by various routes including topically, by injection and by inhalation by mouth or directly into body cavities. Some problems result because the material circulates throughout the body possibly affecting other parts rather than the target area.

The Lungs

Research over the past 3 to 4 decades has revealed the composition and function of the acellular surface film of the lung, the so-called surfactant system. The system is a complex mixture of lipids, proteins and carbohydrates; as described in a recent review: Surfactants and the Lining of the Lung, The Johns Hopkins University Press, Baltimore, 1988. At the alveolar level its function is to prevent excessive accumulation of liquid within the alveolar airspace and to stabilize the alveoli and small-airways against collapse. These functions are achieved principally through the operation of phospholipids at the air/film interface. Whereas certain lung specific proteins of the system may influence this function, it has been widely accepted that fully saturated diacylphospholipids, principally dipalmitoyl phosphatidylcholines (DPPC), impart to the liquid alveolar surface its required biophysical properties (liquid balance and stability against collapse) that sustain normal function. Other fully saturated acyl chain phosphatidyl cholines may also work as well as the saturated diacylphosphatidylglycerols. It is also clear that, whereas lipid composition differs somewhat between alveolar airspace and small airway airspace, the principal phospholipid at each surface is DPPC. Although DPPC is responsible for achieving and maintaining liquid balance and stability in the lung, the addition of spreading agents enhance and assist it in rapidly forming a spread film at the air/liquid surface. Spreading agents are compounds, as listed herein, that assist DPPC in rapidly forming a spread film on the air/liquid surfaces of the lungs and together with DPPC are responsible for achieving and maintaining biophysical properties that enables it to maintain liquid balance and stability in the lungs. There are several compounds that can act as spreading agents, such as cholesteryl esters, (for example: cholesteryl palmitate (CP)); phospholipids (for example:

diacylphosphatidylglycerols (PG),
diacylphosphatidylethanolamines (PE),
diacylphosphatidylserines (PS),
diacylphosphatidylinositols (PI)),
sphingomyelin (Sph) and Cardiolipin (Card)); and virtually any other phospholipid, any of the lysophospholipids; or any of the plasmalogens, dialkylphospholipids, phosphonolipids, carbohydrates and proteins (for example, albumin, pulmonary surfactant proteins A, B; C and D). DPPC is an amphoteric molecule that forms a monomolecular film at the air/lining interface with certain unique properties that explain its normal function: (1) the film, which spreads to cover all surfaces, achieves extremely low surface tension upon compression, e.g., during exhalation, thereby reducing the force that favors liquid movement into the airspace; (2) as airway or alveolar size falls, surface tension falls proportionately, thereby establishing a pressure equilibration among structures to prevent collapse; (3) because of its amphoteric structure, the film can form loose chemical associations with both hydrophobic and hydrophilic moieties and because of its high compressibility these associations can be broken upon film compression, thereby freeing the moiety from the interface; and (4) these loose chemical associations can be modified by the addition of other compounds found in the surfactant system (PG, for example) which can alter the charge distribution on the DPPC molecule, thereby altering the rate at which the moiety (as mentioned in 3. above) is released from the DPPC. DPPC, which is the principal surfactant in all mammalian species examined to date, is synthesized by epithelial cells of the airspaces (the type 2 pneumocyte of the alveoli and an as yet unidentified cell of the airways) and secreted into the acellular lining layer as a variety of "myelin figures", i.e., lipid bilayers in a variety of structural conformations, including multilamellar, tubular myelin and conventional bilayer. It is generally agreed that the myelin figure conformation undergoes a process of unraveling at the air/lining interface, where the monomolecular film configuration is established. Implicit in this scheme of film formation are the concepts of "adsorption" of DPPC at the interface and "spreading" of DPPC at the surface. Other components of the surfactant system, such as CP, PG, PE, PS, PI, other lipidic components (specified herein), carbohydrates and proteins, appear to be important adjuvants (Respir. Physiol. 38:235, 1979; Notter, R. H., Chapt. 2, IN:Pulmonary Surfactant, Elsevier Science Publishers, New York, 1984.): Whereas, DPPC itself is adsorbed relatively slowly to the air/lining interface and, once adsorbed, spreads slowly, both processes are accelerated significantly in the presence of relatively small amounts of spreading agents (like CP, PG, PE, PS, PI and other lipid, carbohydrate and protein components).

DPPC has been administered to infants with respiratory distress syndrome as a therapeutic measure to provide the afflicted infant with the substance, DPPC, in which he is deficient. Attempts have been made at replacement therapy by the use of aerosols, either with FREON propellant directly into a face mask from which the infant breathed, or with an aqueous aerosol generator into a chamber (incubator) in which the infant resided during the course of the disease. Later attempts at surfactant replacement therapy for respiratory distress syndrome include a variety of preparations that are administered (instilled) directly into the airways through an endotracheal tube. These preparations can be classified broadly as either "natural" or "artificial" surfactants. "Natural" surfactants, in general, contain all components of the surfactant system as isolated from human amniotic fluid or from animal lungs (principally bovine and porcine lungs). In these preparations, the isolated components of the surfactant system are suspended in aqueous medium which is then administered as bulk liquid injections into the infants' lungs. "Artificial" surfactants are generally preparations that utilize commercially available synthetic materials. Most preparations are delivered to the infant in bulk liquid suspensions (including liposomes and, in one case, in the form of lipoprotein) and; in another clinical trial a mixture of DPPC:PG was blown into the lungs as dry powder. There have been varying degrees of success reported from the clinical trials of surfactant replacement therapy for treatment of respiratory distress syndrome. Most recently, a variety of phospholipid combinations, including saturated and unsaturated, neutral and polar phospholipids, have been employed in the process of liposome production. In contrast to the use of surfactant for therapeutic purposes (above), the liposomes have been formulated as vehicles to carry medications into the lungs. The liposome is essentially a lipid membrane-bound spherical vesicle, analogous to intracellular organelles, which encapsulates and stores in an aqueous phase the drug(s) to be delivered. Their probable mode of action is by adsorption or fusion to the cell surface, whence either the contents may be liberated and enter the cell by a number of transmembrane routes or the entire liposome may enter the cell by endocytosis. The lamellae that make up the lipid-crystals described herein provide enormous surfaces, e.g., conservatively estimated at 200 micrometers$^2$ for each 0.1 nanogram of phospholipid. Because of the amphoteric and lamellar nature of the crystals, they readily associate with both hydrophilic and hydrophobic molecules, an association that is maintained when these components are resuspended in an aerosol medium. When propelled from the metered-dose nebulizer, the fluorocarbon medium, either chlorofluorocarbon or hydrofluorocarbon, vaporizes rapidly and the DPPC:CP drug, DPPC:PG drug, DPPC:PG:CP drug or DPPC:OTHER COMPONENT(S) drug combination deposits on an aqueous surface, at 37° C., in the crystalline form, which then instantaneously spreads over the surface as an amorphous surface film carrying with it the therapeutic drug for which it serves as a vehicle. Studies in animals have shown quite definitively that the DPPC:CP vehicle is distributed on the lung surfaces uniformly (i.e., there is proportionate distribution to all regions of the lung as shown by radioisotope-tracking experimentally). Each preparation tested spreads rapidly leaving behind a surface film of essentially DPPC that is indistinguishable functionally from the normal surface. Indeed, it is known when lungs are depleted of DPPC experimentally in the laboratory, deposition of the DPPC:CP vehicle can reverse the functional abnormality (see Pediat. Res.,18:404A,1984). The vehicle system for the present invention can deliver but not limited to, for example, 5.0 mg each of DPPC:CP, DPPC:PG or DPPC:CP:PG (200:1, 7:1, or 7:0.35:1, w/w, respectively), which when delivered quantitatively covers 100% of the airspace surface in the lungs of normal adults. In fact, however, delivery is 10% to 85% efficient (depending on nozzle adapter used): Even at 10% efficiency, however, it is estimated that all conducting airway surfaces will receive medication. The amount aerosolized per actuation can be modified by varying the concentration of DPPC to other components in the fluorocarbon propellant(s), the total amount of all components in the fluorocarbon propellants, or the size of the metering valve to yield from 210 micrograms to greater than 25 mg total lipid per actuation. In the vehicles, the concentration of drugs can be varied over a wide range, depending on the drug's characteristics. The ratio of DPPC:OTHER COMPONENT(S) chosen has all the required surface characteristics that render it compatible with normal lung function and suitable as a vehicle for therapeutic drug administration. These advantages include (1) rapid adsorption to the air/liquid interface; (2) rapid spreading at the interface; (3) reduction of surface tension to near-zero; (4) versatile association with both hydrophobic and hydrophilic molecules; (5) delivery of these molecules over a wide surface area; (6) uniform delivery throughout the lung regions; and (7) delivery in sufficient quantity to reach all conducting airway surfaces.

The Eyes

The biophysical characteristics of the DPPC:OTHER COMPONENT(S) drug delivery system that render it suitable for delivery via the pulmonary route also make it suitable for delivery in an ophthalmic aqueous medium.

The composition of the acellular film that covers cornea and conjunctiva (collectively "tear films") is not as well defined as it is for the lungs. The two layers of the tear film are the lipidic layer, secreted primarily by the Meibomian glands, and the underlying aqueous layer, secreted primarily by the accessory lacrimal glands. The lipidic layer, which interfaces with ambient air, serves a number of purposes: (1) It lubricates the juxtaposed conjunctival and corneal surfaces thereby facilitating lid movement (minimizing shear forces) and preventing lid to corneal adherence (anti-sticking). (2) It covers the aqueous layer and thereby minimizes evaporation (tear conservation). (3) With blinking its thickness varies, as conjunctival-corneal surface area changes, while it maintains a continuous film over the aqueous layer (rapid spreading following compression). (4) Following secretion, it spreads rapidly over the entire aqueous surface (rapid adsorption and spreading). (5) Surface tension at the lipid/aqueous interface is low (near-zero) so that fluid dynamics of the aqueous layer are not impeded by the lipidic layer (equilibrium of aqueous flux is practically independent of the lipid layer). (6) When aqueous equilibrium is disturbed (either positive or negative) the simultaneous changes in the local lipid film promote uniform re-distribution of the aqueous layer (geometric uniformity)) The lipid composition (Exptl. Eye Res 15:515, 1973) is roughly sterol esters:wax esters: triglycerides: free fatty acids.

1.1:1:7.8:20.7 (w/w) and other, as yet unidentified lipids. Surface tension at the air/lipid interface is rather high, about 46.2 dynes/cm, and constant.

DISCLOSURE OF THE INVENTION

Broadly contemplated the present invention describes a process for preparing lipid crystals in combination with a therapeutically active substance comprising:

(a) preparing a mixture one or more lipids of the group of phospholipids known as phosphatidycholines and one or more spreading agents, in powder form, and said therapeutically active substance and one or more fluorocarbon propellants, said lipids, spreading agents and therapeutically active substance being insoluble in the propellants; and (b) evaporating the propellants from the mixture.

The present invention uniquely combines dipalmitoyl phosphatidylcholines (DPPC) or any of the other fully saturated acyl chain phospholipids, 80.0 to 99.5% by weight, and other spreading agents, for example phospholipids such as but not limited to PG, PE, PS, PI, lysophospholipids, plasmalogens, dialkylphospholipids, diether phosphonolipids, cardiolipin, sphingomyelin, 0.5 to 20.0% by weight, neutral lipids like cholesteryl esters such as but not limited to cholesteryl palmitate, cholesteryl oleate, cholesteryl stearate, 0.5 to 10.0% by weight, carbohydrates, such as but not limited to glucose, fructose, galactose, pneumogalactan, dextrose, 0.5 to 10.0% by weight, and proteins such as but not limited to albumin, pulmonary surfactant specific proteins A, B, C and D, 0.5 to 10.0% by weight, compounds in lipid-crystalline structures in fluorocarbon (both chloro- and hydrofluorocarbon) propellants in which therapeutically active agents, drugs or other materials can be carried into the lungs after actuation from a metered dose nebulizer. As used throughout the specification and claims, the term "spreading agents" are compounds such as listed herein that assist DPPC in rapidly adsorb and form a spread film on air/liquid surfaces of the lungs and together with DPPC are responsible for achieving and maintaining biophysical properties that achieve liquid balance and stability in the lungs.

The composition defined above, upon addition of water, can then be used either without drugs as an artificial tear, or with drugs as a drug delivery system for the eye, but not limited to the eye. Other advantages will become apparent to those skilled in the art from the Detailed Description, Examples and Claims that follow.

According to the present invention, the above object is met by a process to prepare lipid crystalline figures in fluorocarbon propellants for the delivery of therapeutically active substances which form amorphous films on delivery and which can be suspended in aqueous media to serve as a drug delivery system or, when used without therapeutically active substance, as an artificial tear.

DETAILED DESCRIPTION OF THE INVENTION

In this specification and claims, the term "therapeutically active" includes any substance which is capable of altering a body function, appearance or is a drug; the phrase fluorocarbons includes the class of both chlorofluorocarbons and hydrofluorocarbons; the phrase lipids includes the class of phospholipids including PC, PG, PE, PI and cardiolipins; and the phrase spreading agent includes PG, PE, PS, PI, Sph, Card, lysophospholipids, plasmalogens, dialkylphospholipids, diether phosphonolipids, and all others in the class phospholipid as well as cholesteryl esters (like CP), proteins and carbohydrates.

In this specification and claims the term "spreading agents" are compounds as listed above which assist DPPC in rapidly adsorbing and forming a spread film on air/liquid surfaces and together with DPPC are responsible for achieving and maintaining biophysical properties.

The drug delivery system and artificial tears are comprised of a lipid with a second component being a spreading agent(s), with a third component being the drug to be delivered and a fourth component being fluorocarbons. The major lipid component is the phospholipid 1,2 dipalmitoyl, phosphatidyl choline (DPPC), which is the most surface active of the phospholipids, or any of the fully saturated acyl chain phospholipids. Another, minor, lipid component that also acts as a spreading agent for the major component can be diacylphosphatidylglycerol (PG). The number of carbon atoms in the acyl chains (R and R', see PG formula below) can vary between 8 and 22 and may or may not be fully saturated.

DPPC and PG can be synthesized. They are phospholipids, a class of organic compounds that are the main constituents of cells and are extractable by nonpolar solvents, i.e., chloroform, ether, acetone. DPPC's structural formula is:

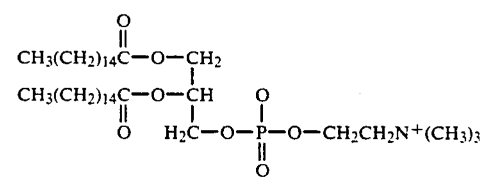

and of PG is:

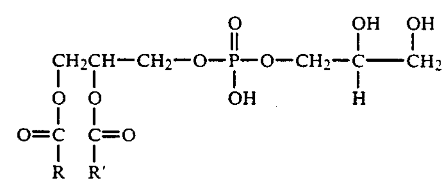

Phospholipids may be obtained commercially in a highly purified form from Fluka Chemical Co. of Ronkonkoma, N.Y.; Sigma Chemical Co. of St. Louis, Mo.; and Avanti Polar Lipids of Birmingham, Ala.

The DPPC and spreading agents are preferred component(s) of both the drug delivery system and artificial tears, and DPPC is present in the composition over a fairly wide range. Percentages of DPPC may be as low as 80% and as high as 99.5% of the lipids by weight with little change in in-vitro properties, however, 99.5% DPPC by weight is preferred.

Another lipid component of the drug delivery system and artificial tears can be cholesteryl palmitate (CP), which also serves as a spreading agent. This cholesteryl ester is a neutral lipid which belongs to a class of organic compounds that are also cell constituents and are extractable by nonpolar solvents such as chloroform, methanol, ether, etc. The structural formula of CP is:

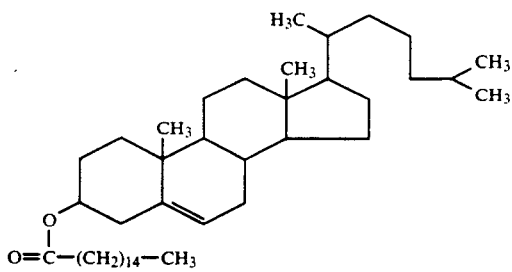

CP may be obtained commercially in a highly purified form from Fluka Chemical Co and Sigma Chemical Co. The CP component constitutes a minor portion of the composition, since it is present in an amount ranging from 0.5% to 10% by weight of the composition. Also the preferred ratio of DPPC to CP is 99. DPPC to 0.5% CP by weight. However, the percentages may be altered within that range without undue interference in desired properties needed for drug delivery and to achieve the desired zero surface tension. The mixture of 90 micrograms of albuterol, purchased from Schering pharmeceuticals, Kenilworth, N.J. in 2mg PC:CP/spray appears to be the preferred combination.

The fluorocarbon propellants, namely:
trichlorodifluoromethane,
dichlorodifluoromethane, and
tetrafluoroethane or mixtures thereof, which are commercially available from Union Carbide Corp., Danbury, Conn. and Armstrong Laboratories West Roxbury, Mass., are usually used for the formation of the lipid crystalline figures of the drug delivery systems and artificial tears. The fluorocarbon propellants are present over a range of 2 to 20 times, by weight, the amount of lipid, but the components of lipid and fluorocarbon propellants are needed to obtain the required lipid crystalline figures.

The artificial tears requires that the lipids in fluorocarbon propellants be solubilized in propylene glycol, available from Union Carbide Corp., after the propellants have evaporated. Because of the hydrophobic nature of the lipids, the use of propylene glycol is helpful in effectively suspending the lipid crystals in aqueous ionic, buffered medium required for delivery to the eye.

The final component of the drug delivery system is the particular drug to be delivered. The amphoteric nature of the major component, i.e., DPPC, makes it capable of carrying any drug or therapeutic agent. The presence of a charge on other lipid components (a negative charge on PG, for example) would alter and improve the carrying capacity of the lipids for a particular therapeutic agent. The composition of the aerosol drug delivery system uses the bronchodilator albuterol in the preparation examples set forth below.

EXAMPLE I

The aerosolized drug delivery system was prepared from chromatographically pure (greater than 99%) DPPC and CP. Both materials were purchased from suppliers on the commercial market where they are available from several chemical supply houses. Specifically, the DPPC and CP were purchased from Sigma Chem., St. Louis, Mo. All purchased materials were checked for purity by standard chromatographic analysis. The Albuterol-$SO_4$ can be purchased from Schering Pharmaceuticals or Glaxo Pharmaceuticals. The materials were then prepared in the fluorocarbon propellants which are also commercially available.

The DPPC and CP were mixed in the dry powder form in a weight ratio of 200:1 (DPPC:CP). To this was added Albuterol-$SO_4$ 200:1:0.09 by weight. Then 5 gms of this mixture was suspended in 55 gms of the first propellant, trichloromonoflurometbane (P11) and subdivided into 30 ml Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids that are insoluble in the propellants. The bottles were immersed in a water-bath to test for leaks, and then fitted with a Valois oral inhalation adapter. The suspension was homogeneous. After standing at room temperature for about three days, a pellicle forms on top of the propellants but was easily resuspended by gentle shaking. The size of the metering valve can be varied to deliver from 1 mg up to 5.4 mg of the DPPC:CP:albuterol mixture. Purity of the components was retained, microbe-free, for at least one year after preparation.

EXAMPLE II

The aerosolized drug delivery system was prepared from chromatographically pure (greater than 99%) DPPC and CP. Both materials were purchased from suppliers on the commercial market where they are available from several chemical supply houses. Specifically, the DPPC and CP were purchased from Sigma Chem., St. Louis, Mo. All purchased materials were checked for purity by standard chromatographic analysis. The Albuterol-$SO_4$ can be purchased from Schering Pharmaceuticals or Glaxo Pharmaceuticals. The materials were then prepared in the fluorocarbon propellants which are also commercially available.

The DPPC and CP were mixed in the dry powder form in a weight ratio of 200:1 (DPPC:CP). To this was added Albuterol-$SO_4$ 200:1:0.09 by weight. Then 25 gms of this mixture was suspended in 55 gms of the first propellant, trichloromonoflurometbane (P11) and subdivided into 30 ml Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids, which are insoluble in the propellants. The bottles were immersed in a water-bath to test for leaks, and then fitted with a Valois oral inhalation adapter. The suspension was homogeneous. After standing at room temperature for about three days, a pellicle forms on top of the propellants but was easily resuspended by gentle shaking. The metering valve size can be varied to deliver from 1 mg up to 5.4 mg of the DPPC:CP:albuterol mixture. Purity of the components was retained, microbe-free, for at least one year after preparation.

EXAMPLE III

The aerosolized drug delivery system was prepared from chromatographically pure (greater than 99%) DPPC, PG and CP. All materials were purchased from suppliers on the commercial market where they are available from several chemical supply houses. Specifically, the DPPC, PG and CP were purchased from Sigma Chem., St. Louis, Mo. All purchased materials were checked for purity by standard chromatographic analysis. The albuterol-$SO_4$ can be purchased from Schering Pharmaceuticals or Glaxo Pharmaceuticals. The materials were then prepared in the chlorofluorocarbon propellants which are also commercially available.

The DPPC, PG and CP were mixed in the dry powder form in a weight ratio of 7:1:0.35 (DPPC:PG:CP). To this was added Albuterol-$SO_4$ 7:1:0.35:00315 by weight. Then 5 gms of this mixture was suspended in 55 gms of the first propellant, trichloromonofluromethane (P11) and subdivided into 30 ml Wheaton plastic-coated glass bottles with a 20 mm neck finish. Valois metering valves were crimped onto each bottle through which 40 gms of the second propellant, dichlorodifluoromethane (P12), was passed. The filled bottles were then gently shaken to disperse the solids, which are insoluble in the propellants. The bottles were immersed in a water-bath to test for leaks, and then fitted with a Valois oral inhalation adapter. The suspension was homogeneous. After standing at room temperature for about three days, a pellicle formed on top of the propellants but was easily resuspended by gentle shaking. The size of the metering valve can be varied to deliver from 1 mg up to 5.4 mg of the DPPC:PG:CP:albuterol mixture. Purity of the components was retained, microbe-free, for at least four months after preparation.

EXAMPLE IV

The aerosolized drug delivery system was prepared from chromatographically pure (greater than 99%) DPPC, PG and CP. All materials were purchased from suppliers on the commercial market where they are available from several chemical supply houses. Specifically, the DPPC, PG and CP were purchased from Sigma Chem., St. Louis, Mo. All purchased materials were checked for purity by standard chromatographic analysis. The Albuterol-$SO_4$ can be purchased from Schering Pharmaceuticals or Glaxo Pharmaceuticals. The materials were then prepared in the hydrofluorocarbon propellants which are also commercially available.

The DPPC, PG and CP were mixed in the dry powder form in a weight ratio of 7:1:0.35 (DPPC:PG:CP). To this was added Albuterol-$SO_4$ 7:1:0.035:0.00315 by weight. Then 5 gms of this mixture were suspended in 95 gms of the hydrofluorocarbon propellant, tetrafluoroethane, and subdivided into 30 ml Wheaton plastic-coated glass bottles with a 20 mm neck finish. Valois metering valves were crimped onto each bottle. The filled bottles were then gently shaken to disperse the solids, which are insoluble in the propellants. The bottles were immersed in a water-bath to test for leaks, and then fitted with a Valois oral inhalation adapter. The suspension is homogeneous. After standing at room temperature for about one day, a pellicle formed on top of the propellants but was easily resuspended by gentle shaking. The size of the metering valve can be varied to deliver from 1 mg up to 5.4 mg of the DPPC:PG:CP:albuterol mixture. Purity of the components was retained, microbe-free, for at least four months after preparation.

The composition of the artificial tears and the drug delivery system for the eyes is identical except for the addition of drug. The artificial tears will be set forth in Example IV and the drug delivery system for the eyes will be set forth in Example V.

EXAMPLE V

Chromatographically pure DPPC and CP (99% pure) may be obtained from Avanti Polar Lipids Co. of Birmingham, Ala., Sigma Chemical Co. of St. Louis, Mo.

DPPC and CP were mixed in a weight ratio of 200:1 and combined with only the fluorocarbon propellants as in Examples I, II or III. Then 5 mg of the mixture were aerosolized into a container, the chlorofluorocarbon or hydrofluorocarbon propellants allowed to evaporate and the DPPC:CP crystals remaining were dissolved in 13 mg of propylene glycol. To this was then added 20 ml of distilled water. The final mixture was heated to 50° C. and gently sonicated for 30 minutes. The artificial tears were then packaged in 15 ml drop dispensers.

The suspension is homogeneous. After standing for about 15 minutes at room temperature the suspension settles out on top of the aqueous phase but was easily resuspended by gentle shaking. The purity of the components was retained for at least seven months after preparation.

EXAMPLE VI

Chromatagrophically pure DPPC and CP (99% pure) were obtained from Avanti Polar Lipids and the other companies previously listed.

DPPC and CP were mixed in a weight ratio of 200:1. To 5 mg of this mixture was added 100 mg of the drug Pilocarpine-HCl for delivery. This final mixture will ultimately result in a 1% solution of the drug when water is added. Pilocarpine-HCl can be purchased as Isotocarpine-HCl from Alcon Pharmaceuticals. Next, the fluorocarbon propellants were added to the mixture as outlined in Examples I, II or III. The mixture was atomized and the fluorocarbon propellants were allowed to evaporate. The 105 mg of the resulting mixture of DPPC:CP:Pilocarpine-HCl were dissolved in 50 mg of propylene glycol to which was added 20 ml of distilled water. The final mixture was heated to 45° C. and gently sonicated for 30 minutes. The drug delivery system for the eyes was then packaged in 15 ml drop dispensers.

The suspension is homogeneious. After standing for about 15 minutes at room temperature the suspension settled out on top of the aqueous phase but was easily resuspended by gentle shaking. The purity of the components was retained for at least seven months after preparation.

Administration of Aerosol Drug Delivery System

The administration of the preparation as an aerosolized drug delivery system, prepared as described in Examples I, II, III, IV, V and VI above, delivers any drug or therapeutic agent by inhalation of the aerosol directly into the lungs, to the dermal, ophthalmic, and mucous membranes and tissues such as but not limited to the hair, skin, nose, mouth, rectum, vagina, urethra, and throat. Test results follow.

Aerosol Characteristics

The diameter of aerosol particles was determined in a cascade impactor. Flow through the impactor was the same as aerosol flow from the nebulizer, 200 microliters/second. All of the particles were equal to or less than 16 microns in diameter. About 95% of the particles were equal to or less than 4 micron in diameter; the diameter of half of these was 1 micron. Mean particle diameter was 1.75±0.25 micron.

Structural characteristics after deposition were assessed by capturing the aerosolized particles on standard scanning electron microscopic grids fixed to glass slides, 22° C., dry. The lipids deposited on glass both as dry particles and as coalesced droplets. The latter evaporated immediately leaving dry lipid. The dry lipids were fixed in osmium vapor ($OsO_4$), coated and viewed with a scanning electron microscope. Crystalline figures, about 100 angstroms thick, were grouped in clumps on the dry surface. This is a unique configuration.

Impaction of the aerosolized crystalline figures on a liquid surface (normal saline solution, NSS) at 37° C., 100% humidity, in a surface balance resulted in a rapid spreading of a principally amorphous film that covered the entire surface (18.1 $cm^2$). Surface tension of the film was measured during expansion and compression at 37° C., 100% humidity. Film expansion to 110.4 $cm^2$ produced a surface tension of 72 dynes/cm and compression to 18.1 $cm^2$ lowered surface tension to less than 1 dyne/cm.

Delivery Of Aerosol To The Lungs

Initially the nozzle of the inhalation adapter was fitted directly to a 3.5 French Portex endotracheal tube (ETT), so that the aerosol traversed the length of the ETT before reaching the airways. It was found that greater than 85% of the aerosol lipids deposited on the ETT and, therefore the apparatus was modified as follows:

A 15 cm polyethylene extension tube (2 mm o.d., 0.5 mm i.d.) was bonded to the nozzle of the inhalation adapter for insertion through an ETT. Metered doses of aerosol delivered from the extension tube contained 5 mg DPPC per actuation with no deposition on the ETT. This was the delivery system used in the study on isolated, entubated rabbit lungs. The aerosol drug delivery system can be used with or without the extension nozzle depending upon the condition of the subject, i.e., whether or not the subject can effectively inhale without assistance.

To test delivery into the lungs, anesthetized (phenobarbital, 30 mg/kg) adult rabbits were sacrificed by exsanguination and the lungs removed. An ETT was inserted to 1 cm above the carina. The extension tube from the aerosol generator was passed to <0.5 cm beyond the ETT. For these studies $^{14}C$-DPPC was added to the usual suspension. With the lung at resting volume, five actuations from the aerosol generator were delivered at 1 minute intervals. Tracheal pressure increased by less than 4 cm $H_2O$ during each actuation. The ETT was removed and the lungs were lavaged with NSS five times. Pooled lavage fluid was analyzed for $^{14}C$ activity in a scintillation counter. The ETT was also rinsed with NSS and analyzed the same way. It was found that 74.6±5.2% of the activity was recovered in the lung lavage fluid, 2.8±0.17% was recovered from the ETT, and 22.6±1.3% remained in the lung.

Intrapulmonary Distribution Of Aerosol

In order to determine intrapulmonary distribution, lungs were flash frozen and dissected after delivery of $^{14}C$-DPPC labeled aerosol. Each lobe was sectioned into pieces between 0.15 and 0.6 gm, dissolved in Protosol and counted for $^{14}C$ activity. Distribution was as follows: right upper lobe 0.5%, right middle lobe 39.6%, right lower lobe 21%, left upper lobe 22%, left lower lobe 3.8%, and trachea plus major airways 32.9%. Distribution was further broken down to 71% central and 29% peripheral, not including the major airways. Histologic survey of the lungs showed no significant changes from control in aerosol treated lungs.

Effect Of Aerosol On Pulmonary Mechanics

Lungs were excised from normal rabbits as described previously. The trachea was cannulated with a Portex ETT to approximately 10 mm above the carina. After degassing in a partial vacuum, volume-pressure (V-P) diagrams were recorded during stepwise inflation-deflation of the lungs between atmospheric (P0) and 30 cm $H_2O$ distending pressure (P30). Each pressure step was 5 cm $H_2O$, with a 2 minute pause between pressure steps. Three cycles were recorded; the third being used for comparisons. There were no further interventions in the control group. Prior to the third cycle, the placebo group received 5 actuations from the aerosol generator containing fluorocarbon propellants without mixture. The same protocol was followed in the treatment group, except that the mixture was aerosolized into the lungs prior to the third cycle. Intratracheal pressure changed insignificantly (less than 1 cm $H_2O$) during each actuation. The V-P diagrams recorded from each group were essentially the same. Only the volume in the treatment group at P0, end deflation was higher than the other groups.

Artificial Tears And Drug Delivery System For The Eye

The administration of the composition as an artificial tear and a drug delivery system for the eyes (prepared as described in EXAMPLES IV and VI above) is intended to serve as a tear replacement in dry eye syndromes and as a delivery system, by drops, for any drug into the eyes.

Characteristics

The surface tension lowering characteristics of the artificial tears/drug delivery system for the eyes was tested on a surface balance. Maximum surface area of 110 $cm^2$ required addition of 18 drops of the composition to simulate the addition of 3 drops into an eye having a surface area of approximately 25 $cm^2$. The surface was allowed to equilibrate and then was compressed and expanded repeatedly at a rate of 20 sec./cycle. Minimum surface tension after the first cycle was 28 dynes/cm. A minimum surface tension of 0 dynes/cm was achieved after about 1 minute of cycling. When cycled at faster rates, which approximate a blink, minimum surface tension was between 5 and 10 dynes/cm.

The composition does not irritate mucus membranes in the mouth, nose or eyes and is non-toxic.

We claim:

1. A process for preparing lipid crystals in combination with a therapeutically active agent comprising:
   (a) preparing a mixture of one or more lipids and one or more spreading agents selected from the group consisting of cholesteryl esters, phospholipids, carbohydrates, and proteins, in powder form; the therapeutically active agent; and one or more fluorocarbon propellants, said lipids, said spreading agents, and said therapeutically active agent being insoluble in the propellants wherein the lipids are present in an amount of about 80 to 99.5 percent by weight and the spreading agents are present in an amount of about 0.5 to about 20 percent by weight, both based on the weight of the mixture; and (b) evaporating the propellants from said mixture.

2. The process defined in claim 1 wherein, simultaneously with or after step (b), the product of the process is delivered to the point of use.

3. The process defined in claim 1 wherein the lipids are phospholipids, neutral lipids, or mixtures thereof.

4. The process defined in claim 3 wherein the phospholipids are any of the class known as phosphatidylcholine.

5. The process defined in claim 4 wherein the phosphatidylcholine is any fully saturated diacyl phosphatidylcholine.

6. The process defined in claim 1 wherein the phospholipid is a diacylphosphatidylglycerol.

7. The process defined in claim 1 wherein the phospholipid is a diacylphosphatidylethanolamine.

8. The process defined in claim 1 wherein the phospholipid is a diacylphosphatidylserine.

9. The process defined in claim 1 wherein the phospholipid is a diacylphosphatidylinositol.

10. The process defined in claim 1 wherein the phospholipid is a sphingomyelin.

11. The process defined in claim 1 wherein the phospholipid is Cardiolipin.

12. The process defined in claim 1 wherein the phospholipid is a lysophospholipid.

13. The process defined in claim 1 wherein the phospholipid is a plasmalogen.

14. The process defined in claim 1 wherein the phospholipid is a diether phosphonolipid.

15. The process defined in claim 1 wherein the phospholipid is a dialkylphospholipid.

16. The process defined in claim 1 wherein the carbohydrates are glucose, fructose, galactose, pneumogalactan, or dextrose.

17. The process defined in claim 1 wherein the protein is selected from albumin and pulmonary surfactant specific proteins A or B or C or D or mixtures thereof.

18. The process defined in claim 1 wherein the cholesteryl ester is cholesteryl palmitate, cholesteryl oleate or cholesteryl stearate.

19. The process defined in claim 1 wherein the fluorocarbon propellants are cholorfluorocarbons, hydrofluorocarbons or mixtures thereof.

20. The product of the process defined in claim 1 wherein about 95% of said product particles are equal to or less than 16 microns in diameter.

* * * * *